United States Patent [19]
Bielsten et al.

[11] 3,980,947
[45] Sept. 14, 1976

[54] METHOD OF ENERGIZING A MAGNETIC STRESS TRANSDUCER TO REDUCE THE CREEP OF THE MEASURING SIGNAL

[75] Inventors: Nils Ove Bielsten; Orvar Dahle; Ronald Grek, all of Vasteras; Bertil Hoffman, Kolback; Sture Siby; Ake Widehn, both of Vasteras, all of Sweden

[73] Assignee: Allmanna Svenska Elektriska Aktiebolaget, Vasteras, Sweden

[22] Filed: May 1, 1975

[21] Appl. No.: 573,797

[30] Foreign Application Priority Data
June 20, 1974 Sweden .............................. 7408157

[52] U.S. Cl. .......................... 324/34 ST; 73/88.5 R; 73/DIG. 2
[51] Int. Cl.² ......................................... G01R 33/18
[58] Field of Search ......... 324/34 R, 34 ST, 34 MA; 73/88.5 R, DIG. 2; 310/26; 336/20

[56] References Cited
UNITED STATES PATENTS

| | | | |
|---|---|---|---|
| 2,912,642 | 11/1959 | Dahle | 324/34 ST |
| 3,424,007 | 1/1969 | Pasnak et al. | 73/DIG. 2 |
| 3,639,832 | 2/1972 | Goebbels | 324/34 R |

FOREIGN PATENTS OR APPLICATIONS 1,297,890  6/1969  Germany ......................... 324/34 ST

*Primary Examiner*—Robert J. Corcoran

[57] ABSTRACT

In measuring mechanical stresses in an object of hardened and tempered steel with a magnetic transducer of the type which comprises a magnetizing circuit for generating a magnetic field in the object and a measuring circuit for sensing the changes in the magnetic field which occur in the object when it is subjected to mechanical forces, in order to reduce the creep of the measuring signal which occurs in the case of continuous feeding, the magnetizing circuit is energize with energy in the form of AC pulses of a pulse length between 20 and 120 milliseconds.

2 Claims, 3 Drawing Figures

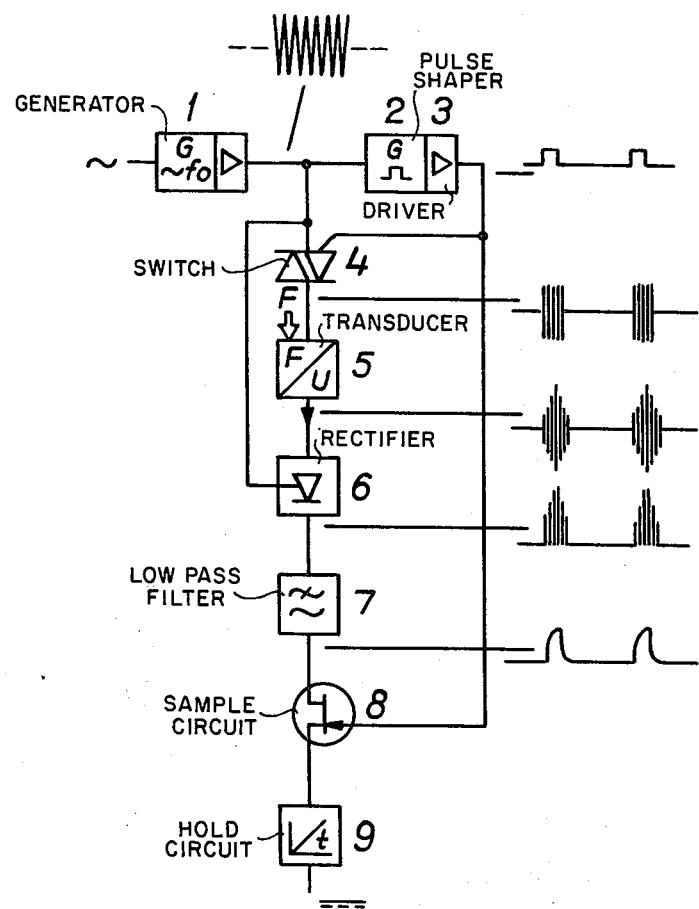

METHOD OF ENERGIZING A MAGNETIC STRESS TRANSDUCER TO REDUCE THE CREEP OF THE MEASURING SIGNAL

BACKGROUND OF THE INVENTION

1. Field of the Invention

The present invention relates to a method of measuring mechanical stresses in measuring objects of hardened steel using magnetic transducers of the type which comprises a magnetizing circuit for generating a magnetic field in the measuring object and a measuring circuit for sensing the changes in the magnetic field which occur in the object being measured when the object is subjected to mechanical forces.

2. The Prior Art

A transducer of this type is shown and described in U.S. Pat. No. 2,912,642.

Normally a transducer of the type shown and described in U.S. Pat. No. 2,912,642 is used for measuring the torque on the propeller shafts on board ships. Such shafts normally have a carbon content of about 0.4% and are in most cases normalized. The internal structure is then composed of ferrite and pearlite, which are both ferromagnetic. As a rule a well-defined connection between stresses in the shaft surface, that is, the torque, and the output signal of the transducer is obtained for such steel. In exceptional cases a so-called creep may be observed. By creep is meant that the signal is to some extent time-dependent so that, after an instantaneous change in the torque, a certain time — of the order of magnitude of a few seconds up to about 1 hour — elapses before the signal has become stable. For soft steel the creep, when it occurs, is positive, that is, the delayed part of the signal change has the same direction as the immediate change. The rate of the creep, that is, the relation between the delayed and the immediate signal change, in this case seldom exceeds a few tenths per cent.

If, on the other hand, the transducer of the above patent is used for measuring shear stresses occurring because of torsion or bending in hardened steel shafts, a negative creep of the signal will occur and this creep is of the order of magnitude of 1% at full magnetization. At low magnetization the creep will disappear, but the neutral point is instead very sensitive to any momentary increase in the magnetization, either caused by an intentional momentary increase of the current, or in the form of a transient current increase caused by a momentary interruption in the exciting current.

SUMMARY OF THE INVENTION

According to the present invention, the creep is reduced to such a degree that it does not disturb the measurements by energizing the magnetizing circuit with energy in the form of AC pulses, preferably of a length between 20 and 120 milliseconds. It has been found that the use of such pulses below a given value results in reducing substantially the creep of the measuring signal which occurs in the case of continuous energization to a value which is acceptable from the point of view of accuracy of measurement.

BRIEF DESCRIPTION OF THE DRAWINGS

To facilitate the understanding of the theory behind the invention and to explain the equipment used in the application of the invention, reference is made to the following drawings:

FIG. 3 shows an example of the feeding and signal processing circuits of a transducer used in the application of the invention.

DESCRIPTION OF THE PREFERRED EMBODIMENTS

Figure 1:
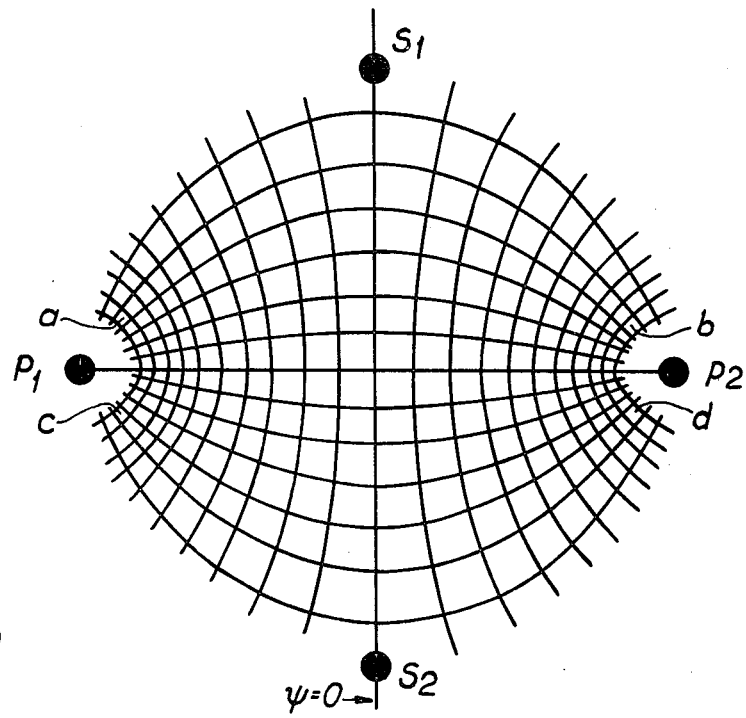
FIG. 1 shows the field configuration in the object being measured in unloaded state.

For an explanation of the creep phenomenon discussed above, reference is made to the accompanying FIGS. 1 and 2 which show the magnetic field at the surface of the measuring object in front of the transducer in unloaded (FIG. 1) and in loaded (FIG. 2) state. The field configuration in FIG. 1 shows H-lines and the magnetic equipotential ($\Psi$) lines are directed at right angles to the H-lines. The areas $a$, $b$, $c$ and $d$ have the greatest importance for the output signal since the field here has its maximum value and is parallel to one of the principal stresses $+\sigma$ or $-\sigma$. Changes in the permeability in these areas because of the principal stresses will control the skewing of the zero equipotential line $\Psi=0$ from the position in FIG. 1 to the position in FIG. 2, and consequently determine the magnetic potential difference between the two secondary poles $S_1$ and $S_2$ of the transducer, that is, the output signal of the transducer.

If the momentary increase of the exciting current occurs the first time at zero load, nothing will happen according to the theory which will be put forward in the following.

If a momentary current increase occurs at full load, for example, this will result in a shifting of the zero signal in the negative direction by several per cent. Thereafter the shaft is no longer insensitive in the unloaded state. A momentary current increase will now result in a positive shifting of the zero signal.

Since these effects are manifest only on hardened steel, they must be caused by special properties in the structure of such material. Besides the hardness, the most characteristic property from the magnetic point of view is that there are a few per cent of untransformed austenite enclosed in the structure of more or less tempered martensite. Thus, there exists a two-phase system consisting of, say, 95% magnetic phase and 5% non-magnetic phase. The fit in the boundary area between the two types of crystal must be very bad since the magnetic phase has a body centered, basically cubic lattice, whereas the non-magnetic phase has a face-centered cubit lattice with a different lattice constant. It is therefore quite normal for the boundaries between the phases to have more viscous properties than normal crystal boundaries.

When a material of this kind is magnetized, the magnetic phase is subjected to magnetostriction, that is, it tends to extend in the field direction, an effect that the non-magnetic phase tends to prevent. The compression stress which is caused by the partly prevented magnetostriction is relieved to a certain extent by slip at the phase boundaries. All this results in a residual tensile stress when the magnetization is reduced to zero or to a low value. With AC magnetization, which is used in the transducer, the magnetostriction which is independent of the sign of the magnetizing current will have the same characteristics as a rectified current, that is, it is composed of a "DC component" with a superimposed "AC component" with a doubled frequency. It is of course basically the "DC component" that causes the slip and thus the residual tensile stress, but the "AC component" probably also has a contributing effect in the same way as vibration in case of macroscopic friction.

If we apply these conclusions to the virginal, unloaded case according to FIG. 1, we will obtain equal residual tensile stresses in the field direction in the four controlling areas, a, b, c, d, which would not result in any change in the zero signal.

Figure 2:
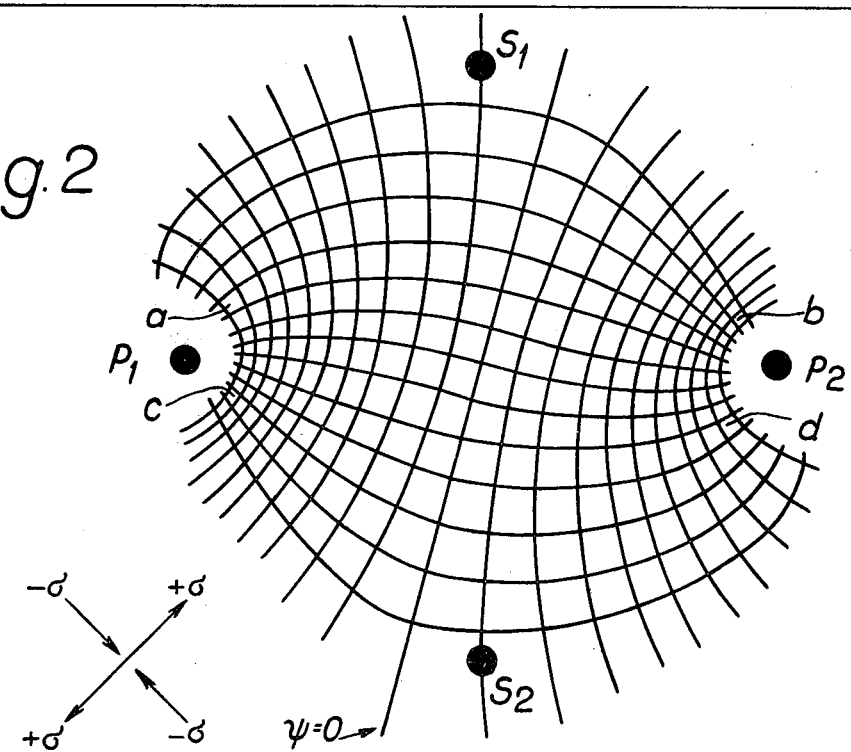
FIG. 2 shows the field configuration when the object being measured is influenced by a mechanical force.

For the loaded case, FIG. 2, the conditions will be quite different. In the areas a and d, where the field lies in the direction of tension, the domains are to a great extent already aligned in this direction by the tension. This reduces the magnetostriction considerably in these areas and thus also the residual tensile stress after a momentary increase in the magnetization. In the areas b and c, on the other hand, where the field direction coincides with the direction of compression, the stress will align the domains perpendicular to the field, whereby the magnetostriction is considerably increased and the residual tensile stress is also increased after a momentary magnetization increase. After unloading, the field pattern acquires a reversed character compared with FIG. 2, which results in a negative change in the zero signal.

In this non-virginal unloaded state, the residual tension is thus lower in the areas a and d (with tension in the field direction when loaded) than in the areas b and c (with compression in the field direction when loaded). Upon a momentary increase in the magnetization, the magnetostriction is therefore higher in the areas a and d, which results in larger slip and thus in a greater increase in the residual tension in these areas than in the areas b and c. The momentary magnetization increase therefore results in a positive change of the zero signal in this case.

This disturbing instability in the zero signal versus transitory current pulses generated, for example, by momentary interruptions in the magnetizing circuit, can be eliminated by a strong increase of the magnetization. As mentioned earlier, the slip in the viscoelastic boundaries between the magnetic and non-magnetic phases will now instead become noticeable as a negative creep in the loaded state and a corresponding, positive-going creep in the unloaded state. This can be explained by the same reasoning as has been used to explain the change in the zero point in case of a momentary increase in a normally low magnetization. The difference is mainly that, in case of a short increase in a normally low magnetization, it is the hysteresis in the elastic component of the grain boundary slip that is important. In case of a high continuous magnetization, it is instead the viscous component of the slip that is noticeable.

Fortunately enough, at least the viscous part of the grain boundary slip, which gives rise to creep in the signal in case of a high magnetization, seems to need a certain minimum starting time to develop. Therefore, according to the invention, the transducer is magnetized by short pulses of AC current instead of continuous alternating current which was customary before. The pulse length should be less than a critical value which depends on the material of the object being measured. When testing a material of tool steel type, the creep was reduced from about 1% to less than 0.1% by magnetization of the transducer by AC pulses of a length of between 20 and 120 milliseconds and a frequency of 400 Hz. The pulse time is chosen with regard to the material in the measuring object so that the slip cannot develop so far that the creep of the measuring signal caused by this slip interferes with the measuring. This stabilization of the zero signal is achieved even if the pause between the pulses is not longer than the pulse time. This shows that it is not only a question of an increase in the time constant when the current is pulsed.

FIG. 3 shows a functional diagram of a pulse-feeding system according to the invention.

An excitation unit 1 generates an alternating voltage with a constant frequency $f_o$ which may be, for example, 400 Hz. A pulse shaper 2 generates pulses of a definite length, pulse repetition frequency and phase synchronism. These pulses control an electronic switch 4 by way of a driver 3, said switch 4 connecting the output of the excitation unit 1 with the magnetizing winding of the transducer 5.

The signal processing unit consists of a phase sensitive rectifier 6 controlled by the frequency $f_o$ and followed by a low pass filter 7. The peak value of the signal pulses is sensed by a sample and hold circuit 8 and 9 controlled by the pulse shaper 2. A direct voltage signal occurs on the output 9 of the sample and hold circuit, said signal being proportional to the sensed stress.

If several transducers are included in a measuring system, they can be magnetized consecutively in a certain sequence from the same excitation circuit by way of switches which connect the transducers to the excitation circuit in a fixed time sequence. The signal processing device may consist of one channel for each transducer, in the same way as shown in FIG. 3, or of one single channel which is connected by a multiplexar to the transducer which is magnetized at the time.

We claim:
1. Method for measuring mechanical stresses in an object of hardened and tempered steel using a magnetic transducer of the type which comprises a magnetizing circuit for generating a magnetic field in the object and a measuring circuit for sensing the changes in the magnetic field which occur in the object when it is subjected to mechanical forces, which comprises energizing the magnetizing circuit with electric energy in the form of short pulses of AC current, the pulse length of which is sufficiently low to reduce the creep of the measuring signal to a value which is negligible in comparison with the value of the creep when the magnetizing circuit is energized with continuous AC current.

2. Method according to claim 1, in which the pulse length is between 20 and 120 milliseconds.

* * * * *